United States Patent [19]

Hudson et al.

[11] Patent Number: 5,164,523

[45] Date of Patent: Nov. 17, 1992

[54] PROCESS FOR THE PRODUCTION OF GRANULAR METAL SOAP

[75] Inventors: Clyde R. Hudson, Imperial; Edgar N. Nelson, Chesterfield, both of Mo.

[73] Assignee: Mallinckrodt Specialty Chemicals Company, St. Louis, Mo.

[21] Appl. No.: 711,427

[22] Filed: Jun. 6, 1991

Related U.S. Application Data

[63] Continuation of Ser. No. 251,520, Sep. 30, 1988, abandoned.

[51] Int. Cl.⁵ ............................................. C11C 1/00
[52] U.S. Cl. ................................... 554/75; 554/128
[58] Field of Search ............... 260/413, 414; 554/153, 554/214, 218, 128, 130, 131, 132, 133, 134, 71, 72, 75, 76

[56] References Cited

U.S. PATENT DOCUMENTS

| | | | |
|---|---|---|---|
| 3,476,786 | 11/1969 | Lally et al. | 260/413 |
| 3,803,188 | 4/1974 | Scott et al. | 260/413 S |
| 4,235,794 | 11/1980 | Rieber et al. | 260/413 |
| 4,294,771 | 10/1981 | Pietralla et al. | 260/413 S |
| 4,307,027 | 12/1981 | Borzelli et al. | 260/413 |
| 4,473,504 | 9/1984 | Odashima et al. | 260/414 |

FOREIGN PATENT DOCUMENTS

| | | | |
|---|---|---|---|
| 0004112 | 9/1979 | European Pat. Off. | |
| 3529217 | 12/1987 | Fed. Rep. of Germany | |
| 58-164540 | 9/1983 | Japan | 260/414 |
| 174615 | 11/1965 | U.S.S.R. | 260/414 |

Primary Examiner—Arthur C. Prescott
Attorney, Agent, or Firm—Rothwell, Figg, Ernst & Kurz

[57] ABSTRACT

A fusion process for the rapid production of a granular metal soap passes a mixture of metal (e.g. zinc) oxide, one or more molten fatty acids and a catalyst through a heated reactor to form molten metallic soap which is then ejected through a spray nozzle in a cooling tower to form a granular soap product. Use of a spiral tubular reactor with a rapid heating coil is disclosed. The reaction is conducted under pressure to maintain water generated by the reaction in the liquid state. Flashing of the reaction water in the cooling tower aids in cooling and formation of fine granules.

26 Claims, 1 Drawing Sheet

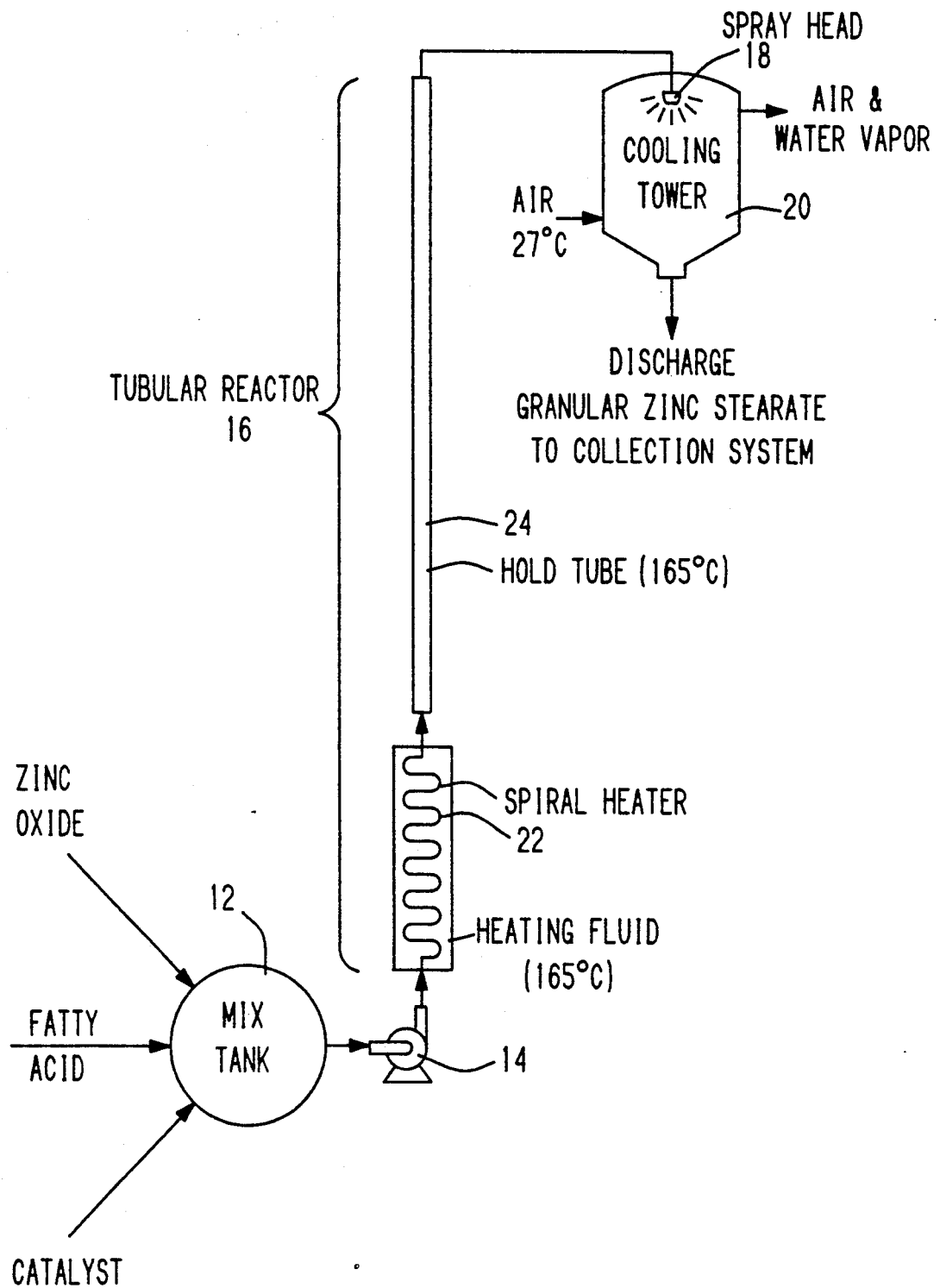

PROCESS FOR THE PRODUCTION OF GRANULAR METAL SOAP

This is a continuation of application Ser. No. 07/251,520, filed Sept. 30, 1988, and now abandoned.

BACKGROUND OF THE INVENTION

1. Field of the Invention

This invention relates to fusion processes for production of granular metal soaps by reaction of metal oxides and higher monocarboxylic acids in the presence of a catalyst.

2. Prior Art

Granular metal soaps such as zinc soaps are used as waterproofing agents, lubricating or anticaking agents and thickening or suspension agents. The soaps also are useful as stabilizing agents for plastics.

The production of granular metal soaps by various processes, including precipitation and fusion processes, is known in the art. Precipitation processes generally produce metallic soap by reaction of an aqueous solution of a water-soluble metal salt and a fatty acid alkali metal salt, whereupon the metal soap precipitates out of solution. These precipitation processes require time consuming filtering, washing and drying steps to isolate a purified product from the aqueous reaction mixture. Fusion processes, however, produce metal soaps by the reaction of metal oxide, hydroxide, carbonate or acetate with a molten fatty acid at temperatures sufficiently high to form the metal soaps, and often avoid the separate filtering, washing and drying steps. Most commercial fusion processes produce large lumps of metal soap which must be ground to a desired size.

U.S. Pat. No. 3,803,188 discloses a process for producing metal soaps by dispersing finely ground metal oxide in molten fatty acid (well below the melting point of the desired soap), adding water and allowing the reaction to proceed (about 10 to 30 minutes) below about 110° C. while stirring. The reaction product is milled to a desired size.

U.S. Pat. No. 4,307,027 discloses a continuous process for the preparation of dry metallic soaps of higher fatty acids in a plug flow reactor. Metal oxides or hydroxides and fatty acids are combined, optionally in the presence of a catalyst such as water, a nonionic emulsifier or a caustic solution, and heated to a reaction-inducing temperature in a stirred tank reactor for 10 to 80 minutes. The heated reactants are continuously fed to a plug flow reactor where they reside for about 2 to 60 minutes. Solid reaction products are continuously discharged from the plug flow reactor and fed to a hammer mill to obtain a coarse ground product. The coarse ground product is fed to a jet mill for further size reduction so that less than 0.1% is retained on 325 mesh.

U.S. Pat. No. 4,294,771 describes a "method for producing metal soaps in dust-free granulate form without any grinding step." Fatty acid, metal oxide, hydroxide or carbonate, and 1 to 5% water (based on the weight of the fatty acid) are heated and agitated in a closed vessel. Temperature and pressure increase as the exothermic reaction proceeds over the course of 10 to 15 minutes. After completion, the added water as well as the reaction water are drawn off under decreased pressure during agitation. A granular soap remains.

Fusion processes generally employ catalysts to produce a more rapid reaction at a lower temperature. Japanese Patent No. 59/170035 discloses the reaction of fatty acids with zinc oxide or calcium oxide in the presence of a polycarboxylic acid such as phthalic acid, citric acid, or succinic acid at 130° C. for 35 minutes.

Prior art fusion processes generally have one or more deficiencies, such as requiring separate grinding steps, using inefficient batch processing techniques, requiring relatively expensive and/or large equipment, having long inefficient reaction times, etc.

It is an object of the present invention to utilize a dry fusion process to rapidly produce a granular metal soap.

SUMMARY OF THE INVENTION

In accordance with the invention, molten metal soap, i.e., a molten metal salt of a higher fatty acid produced by fusion of metal oxide and higher fatty acid in the presence of a catalyst, is ejected through a spray nozzle into a cooling apparatus to form a granular metal soap product.

An advantage of the invention is that a granular metal soap product having a purity and form suitable for direct use is produced with a minimum of steps.

A further advantage is that continuous fusion reaction and production of granular metal soap, without any grinding steps, are made possible.

Further aspects of the invention may include one or more of the following features. The fusion reaction is at a pressure greater than the vapor pressure of reaction product water to maintain the reaction water liquid, while the spraying in the cooling apparatus is at a pressure less than the vapor pressure of the reaction water to flash the reaction water and assist in fine granular soap formation. The fusion reaction is conducted in primary and secondary tubular reactors with respective small and large diameters to provide rapid heating and maintenance, respectively, of reactants to enable complete fusion in five minutes or less.

BRIEF DESCRIPTION OF THE DRAWING

The drawing is a diagrammatic illustration of an apparatus and method for producing zinc soap in accordance with the invention.

DESCRIPTION OF THE PREFERRED EMBODIMENTS

In accordance with one embodiment of the invention illustrated in the drawing, a fatty acid, such as commercial stearic acid, is heated to melt the fatty acid. The molten fatty acid is then mixed in mixer 12 with a metal oxide, such as zinc oxide, and a catalyst, such as azelaic acid. This mixture is then pumped by pump 14 through a spiral tubular reactor 16 where the mixture is heated to its reaction temperature, and the fatty acid and metal are fused to form a molten metal soap. The molten metal soap is then ejected through a spray nozzle 18 into a cooling tower 20 to form a granular metallic soap product which is suitable for use without any further grinding or milling step.

Fatty acids which can be used to produce metallic soaps include higher monocarboxylic acids having from about 12 to about 22 carbon atoms. These higher carboxylic acids are also known as fatty acids. Saturated or unsaturated, substituted or unsubstituted fatty acids are useful. Either a single fatty acid or combinations of various fatty acids may be employed. For example any of lauric acid, oleic acid, linoleic acid, myristic acid, palmitic acid, stearic acid, or linolenic acid, either alone or in combination with any of the other acids may be used. It is understood that other acids not specifically named herein are useful. Commercially available fatty acids such as commercial stearic acid, lauric acid or the like and commercially available blends of fatty acids (including naturally-occurring blends) also are useful in this process. Especially useful in the preferred embodiment is commercial stearic acid which generally consists of 50% to 75% by weight stearic acid (octodecanoic acid), 25% to 50% by weight palmitic acid (hexadecanoic acid), and small amounts, i.e., generally less than 2% by weight, other $C_{12}$–$C_{22}$ aliphatic saturated and unsaturated monocarboxylic acids. Throughout this specification the term fatty acid and higher monocarboxylic acid are used interchangeably. The use of these singular terms does not exclude the use of a plurality of fatty acids.

After the fatty acid initially is melted in step 10, the fatty acid is maintained in the molten state pending further process steps. A melting and holding temperature in the range from about 70° to 75° C. is suitable for commercial stearic acid. Other melting and holding temperatures may be suitable for other fatty acids.

The metal oxide mixed into the molten fatty acid in step 12 is zinc oxide, calcium oxide, or any other metal oxide suitable for use in making metallic soap in accordance with the process. Zinc oxide is used in the described preferred embodiment. The metal oxide is desirably introduced in a mole ratio of about 1:2 with moles of metal oxide will be introduced per mole of fatty acid. Most preferably 0.498 moles of metal oxide will be introduced per mole of fatty acid.

The catalyst mixed with the metal oxide/fatty acid dispersion in step 12 is any catalyst which will induce fusion between the metal oxide and the fatty acid at a lower temperature than would otherwise be possible without introducing material which would interfere with the process or which is undesirable in the product. Preferably, the catalyst provides an induction temperature of from about 125° C. to about 150° C. Examples of such catalysts include dicarboxylic acids having carbon chains of from about 6 to about 9 carbon atoms and aromatic dicarboxylic acids of about 6 to about 9 carbon atoms. Thus, adipic acid, azelaic acid, phthalic acid, isophthalic acid and terephthalic acid are all suitable as catalysts. It is to be understood that other unnamed dicarboxylic acids having from about 6 to 9 carbons are also suitable as catalysts for the present process. An amount of catalyst sufficient to lower the fusion temperature to the desired range is sufficient. Usually the amount of catalyst added will not exceed about 0.1% by weight based on the weight of the metal oxide/fatty acid mixture.

The fatty acid, metal oxide and catalyst components, which preferably include substantially no water, are combined in any convenient sequence. We have found it most convenient to melt the fatty acid component and then mix the metal oxide and catalyst components therein. However, either the metal oxide or catalyst component may be first mixed with the molten fatty acid with the other component added later, or the metal oxide and catalyst components may be mixed with each other before being introduced to the molten fatty acid. Preferably, little water is added to the mixture so that the quantity of water in the molten soap product, including water produced by the reaction and any water in the feed mixture, is easily removed by flashing in the cooling tower.

Reactor apparatuses suitable for use in the inventive method must be capable of quickly raising the temperature of the mixture and maintaining the mixture at elevated pressure during the fusion reaction. Examples include tubular reactors, extruders and plug flow reactors. The reactor 16 illustrated in the drawing is a continuous feed dual stage reactor apparatus having a primary reaction chamber for quickly raising the temperature of the dispersion to induce fusion and a secondary reaction chamber for holding the induced dispersion until fusion is essentially complete. More particularly, the tubular reactor 16 is a spiral tubular reactor which has a primary reactor or heating coil 22 of small diameter tubing having a relatively high surface area per volume ratio, and a secondary reactor coil 24 of much larger diameter tubing. The linear diameter of a hold tube 24 is about five to seven times as large as that of the linear diameter of the spiral heater tube 22. For example, the primary reactor coil 22 is formed from 3/8 inch (0.95cm) diameter tubing having a length of about 20 feet (6m) and having a surface area per volume of about 150 ft$^2$/ft$^2$ (5cm$^2$/cm$^2$), and the secondary tubing 24 is 2 inch (5cm) diameter pipe having a length of about 40 feet (12m). The large surface area to volume ratio of the heating coil 22 enables the incoming mixture to be rapidly and evenly heated to the induction temperature (e.g. 125° to 150° C. with a residence time of about 10 seconds or less in the heating coil 22). The heated reaction mixture flows from the spiral heater 22 into the larger holding tube 24 which is downstream of and in fluid connection with the primary spiral tube 22. The holding tube 24 is heated to maintain the reaction mixture at a temperature of at least as great as the temperature attained in the heater coil 22 and above the melting point of the product soap. For example, the hold tube is maintained at a temperature from about 150° C. to about 170° C. with a residence time of about 5 minutes or less to produce substantially complete fusion of the metal oxide and fatty acid in the reaction mixture, i.e., 1.0% or less by weight free fatty acid content in the product metal soap.

From the reactor 16, the molten metal soap is fed to a spray nozzle 18 which is in fluid communication with the hold tube 24 and which sprays the molten metal soap into a cooling apparatus such as cooling tower 20. The molten metal spray is cooled in the cooling tower 20 to form a granular product which is discharged from the bottom of the cooling tower 20 in a highly pure, ready-to-use form.

The primary coil 22 and secondary coil 24 form a closed reaction chamber between the pump 14 and the spray nozzle 18. The pump 14 maintains a pressure in this reaction chamber greater than the vapor pressure of water produced by the fusion reaction so as to maintain the reaction water in a liquid state. For a reaction temperature of 150°–170° C., the pressure is maintained at 100 psia (690 KPa) or more. The reaction water, finely dispersed throughout the soap product as it is ejected from the spray nozzle, is flashed to its vapor state in the cooling tower 20 which is generally maintained at or slightly above atmospheric pressure and substantially below the vapor pressure of the reaction water at the nozzle exit temperature. The flashing of all reaction water to vapor aids in producing fine soap granules by exploding larger soap droplets ejected from the nozzle 18, and by providing rapid cooling of molten soap particles. The water vapor is removed from soap granules and the cooling tower 20 by the cooling air which is passed through the tower.

The granules produced by the preferred embodiment are predominately minus 40, plus 200 mesh (0.1 to 0.6 mm in diameter), i.e., at least 90% of the product granules have a size in the range from 0.1 to 0.6 mm.

As an alternative to the closed tubular reactor and flashed reaction water, a vented or open reaction chamber may be employed wherein water vapor is removed as it is formed during the reaction. The spray nozzle 18 can be of a type producing the desired soap granule size, for example, an atomizing nozzle where an air stream divides the molten soap stream into a fine particle spray in the cooling tower.

The present process is applicable to widely varying ratios of reactants, allowing easy variations of the chemical properties of finished soap products to include the production of clear melt grade soaps with excellent heat stability. For example, the acid value and choice of fatty acid(s) can be varied. Conducting the fusion reaction completely in the liquid phase, without the use of water, simplifies the equipment and reactor design and eases the processing. No milling is necessary. No isolating, washing or drying steps are needed. The product is clear, uncolored and stable. As exposure to high temperatures, i.e. those above the melting point of the soap, is brief (generally less than about 5 minutes) thermal degradation of the soap is minimized. Thus, soaps produced by this process are particularly heat stable.

The usefulness of the present process also is reflected in the presence of a low percentage by weight of free fatty acids in a finished product. Free fatty acids are defined as those acids which have not fused with metal to become soap, or which have degraded from soap to their free form. Generally, 1.0% or less by weight free fatty acid content in a metal soap is considered acceptable by industry standards. The present process consistently produces metal soaps with a free fatty acid content of less than 1.0% by weight. Additionally, this process produces soaps having a purity of 99%.

The examples set forth below are provided for illustrative purposes and are not to be construed as limiting.

EXAMPLE 1

450 lbs. of zinc oxide is dispersed in 3000 lbs. of molten commercial stearic acid (acid value 207.5) at 75° C. 1.5 lbs. of azelaic acid catalyst is added to the dispersion. This dispersion is pumped at a flow rate of about 0.33 ft$^3$/min. and at a pressure of about 200 psia (1379 KPa) through the tubular reactor apparatus of the drawing. Heating fluid temperatures for the primary and secondary reactor chambers are both set at 165° C. Residence time within the heating coil 22 is approximately 3 seconds during which the dispersion is heated to about 150° C. Residence time within the larger reaction tube 24 is approximately 2.2 minutes with the product soap at the exit having a temperature of about 165° C. The molten reaction product is passed through the spray nozzle 18 and into the cooling tower 20 where water formed by the reaction is flashed. The resulting fine droplets of molten soap are quickly solidified and the granules of soap are collected from the bottom of the cooling tower. The entire process is completed in less than 2.5 minutes. The resulting product is a clear melt, granular, free-flowing product with a free fatty acid content of 0.3%, a bulk density of 35 lbs./ft.$^3$ and excellent heat stability.

EXAMPLE 2

430 lbs. of zinc oxide is dispersed in 2900 lbs. of molten stearic acid (acid value 205) at 75° C. 1.5 lbs. of azelaic acid catalyst is added to the dispersion. This dispersion is pumped through the tubular reactor apparatus as described in Example 1 and through the spray nozzle into the cooling tower at a flow rate of about 0.30 ft.$^3$/min. The reaction is completed in about 2.5 minutes. Residence times in the spiral heater 22 and hold tube 24 are about 3.1 seconds and 2.4 minutes respectively. The resulting product is a clear melt, granular, free-flowing product with a free fatty acid content of 0.8%, a bulk density of 39 lbs./ft.$^3$ and excellent heat stability.

EXAMPLE 3

303 lbs. of zinc oxide is dispersed in 1996 lbs. of molten stearic acid (acid value 210) at 75° C. 1.0 lb. of azelaic acid catalyst is added to the dispersion. This dispersion is pumped through the tubular reactor apparatus as described in Example 1 and through the spray nozzle into the cooling tower at a flow rate of about 0.27 ft.$^3$/min. The reaction is completed in just over 2.6 min. Residence times in the spiral heater and hold tube are about 3.4 sec. and 2.6 min. respectively. The resulting product is a clear melt, granular, free flowing product with a free fatty acid content of 0.4%, a bulk density of 35 lbs./ft.$^3$ and excellent heat stability.

What is claimed is:

1. A continuous process for the rapid production of granular metal soap, comprising:
   (a) forming a mixture consisting essentially of metal oxide, catalyst and molten higher fatty acid;
   (b) reacting the metal oxide and fatty acid to form molten metal soap by passing the mixture through a reactor apparatus, said reacting being performed at a pressure greater than the vapor pressure of reaction water; and
   (c) spraying the molten soap into a cooling apparatus to form solid granules of metal soap, said spraying being performed in the cooling apparatus at a pressure below the vapor pressure of the reaction water so as to flash the reaction water to aid granule formation and separation of the reaction water from the solid granules of metal soap.

2. A process as claimed in claim 1 wherein the metal oxide is zinc oxide.

3. A process of claim 1 wherein step (b) is shed by passing the dispersion through a primary reaction vessel and then through a secondary reaction vessel.

4. A process of claim 3 wherein the primary reaction vessel is a spiral tube heated to a temperature sufficient to induce fusion of the metal oxide and fatty acid.

5. A process of claim 3 wherein the spiral tube is heated to a temperature between about 125° C. and about 170° C.

6. A process of claim 4 wherein the secondary reaction vessel is a hold tube heated to a temperature above the melting point of the soap.

7. A process of claim 4 wherein the secondary reaction vessel is a hold tube heated to a temperature not less than the temperature of the spiral tube.

8. A process of claim 3 wherein the secondary reaction vessel is a hold tube heated to a temperature between about 150° C. and about 170° C.

9. A process of claim 1 wherein step (c) is performed by passing the molten metal soap through the spray nozzle into a cooling tower.

10. A process of claim 2 wherein the catalyst permits fusion to be induced at a temperature of between about 125° C. and 150° C.

11. A process of claim 1 wherein the catalyst is a dicarboxylic acid containing from about 6 to about 9 carbon atoms.

12. A process of claim 10 wherein the catalyst is a dicarboxylic acid containing from about 6 to about 9 carbon atoms.

13. A process of claim 12 wherein the catalyst is azelaic acid.

14. A process of claim 1 wherein said mixture is essentially water-free.

15. A process of claim 1 wherein the granular product has a size predominantly in the range of from 0.1 mm to 0.6 mm.

16. A process of claim 1 wherein said fusing and forming steps are accomplished in a total time o five minutes or less.

17. A process of claim 1 wherein the higher fatty acid contains from about 12 to about 22 carbon atoms.

18. A process for the rapid production of granular metallic soap, comprising:
    (a) providing a mixture consisting essentially of molten higher monocarboxylic acid, metal oxide and catalyst;
    (b) transporting said mixture through a spiral heater tube to rapidly and evenly heat the mixture to a temperature sufficient to induce the molten mixture of metal oxide and monocarboxylic acid to fuse to form a soap;
    (c) transferring said induced mixture from said spiral heater tube to a hold tube heated to a temperature sufficient to maintain said induced mixture, and the soap formed thereof, in a liquid state and to allow substantially complete fusion to soap to occur;
    (d) said transporting and transferring being performed at a pressure greater than the vapor pressure of reaction water;
    (e) spraying said molten soap into a cooling apparatus to remove reaction water from said soap and to produce a granular metallic soap product;
    (f) said spraying being performed in the cooling apparatus at a pressure below the vapor pressure of the reaction water so as to flash the reaction water to aid granule formation and separation of the reaction water from the solid granules of metal soap.

19. A process of claim 18 wherein said metal oxide is zinc oxide.

20. A process of claim 18 wherein said monocarboxylic acid has a carbon chain of from about 12 to about 22 carbon atoms.

21. A process of claim 18 wherein said catalyst is selected to provide a reaction induction temperature of from about 125° C. to about 150° C.

22. A process of claim 21 wherein said catalyst is a dicarboxylic acid having from 6 to 9 carbon atoms.

23. A process of claim 18 wherein the dispersion is maintained at a temperature of from about 70° C. to about 75° C. prior to transport into said spiral heater.

24. A process of claim 18 wherein said hold tube is preheated to a temperature of not less than the temperature in said spiral heater.

25. A process of claim 18 wherein the temperature of said hold tube is sufficient to maintain said induced dispersion and said soap in a liquid state.

26. A process of claim 25 wherein said hold tube is preheated to between about 150° C. and 170° C.

* * * * *

UNITED STATES PATENT AND TRADEMARK OFFICE
CERTIFICATE OF CORRECTION

PATENT NO. : 5,164,523
DATED : November 17, 1992
INVENTOR(S) : Hudson et al.

It is certified that error appears in the above-identified patent and that said Letters Patent is hereby corrected as shown below:

Column 3, line 27, after "with", insert --respect to the fatty acid. Preferably 0.495 to 0.55--.

Column 4, line 20, delete "$ft^2/ft^2$ ($5cm^2/cm^2$)", and insert -- $ft^2/ft^3$ ($5cm^2/cm^3$)--.
Column 6,
Claim 3, line 1, after "is", insert --accompli---.
Column 7,
Claim 10, line 1, change "2", to --1--.

Claim 16, line 2, delete "o", and insert --of about--.

Signed and Sealed this

Fifth Day of October, 1993

*Attest:*

BRUCE LEHMAN

*Attesting Officer*     *Commissioner of Patents and Trademarks*